United States Patent [19]
Aoki et al.

[11] Patent Number: 6,118,030
[45] Date of Patent: Sep. 12, 2000

[54] PROCESS FOR PRODUCING DICHLOROACETOXYPROPANE AND DERIVATIVES THEREOF

[75] Inventors: Takanori Aoki; Takami Ohe; Haruki Ishikami; Taketoshi Naitoh; Tatsuharu Arai, all of Kawasaki, Japan

[73] Assignee: Showa Denko K.K., Tokyo, Japan

[21] Appl. No.: 09/249,781

[22] Filed: Feb. 16, 1999

Related U.S. Application Data

[60] Provisional application No. 60/082,625, Apr. 22, 1998.

[30] Foreign Application Priority Data

| Mar. 31, 1998 | [JP] | Japan | 10-085657 |
| Nov. 20, 1998 | [JP] | Japan | 10-330851 |

[51] Int. Cl.$^7$ .................................................. C07C 31/34
[52] U.S. Cl. ........................... 568/841; 560/266; 549/514
[58] Field of Search ............................ 560/266; 568/877, 568/841; 549/514

[56] References Cited

U.S. PATENT DOCUMENTS

| 2,099,231 | 11/1937 | Ruys et al. . | |
| 3,290,395 | 12/1966 | Bohm | 260/633 |
| 3,801,626 | 4/1974 | Grolig | 260/491 |
| 5,345,003 | 9/1994 | Wananabe | 204/157.9 |

FOREIGN PATENT DOCUMENTS 52-16091  5/1977  Japan .

OTHER PUBLICATIONS

Chemical Abstracts, vol. 97, No. 24, Dec. 13, 1982: Columbus, Ohio. Abstract No. 199832d, Grigorev AA. et al.: "Allyl Acetate as a Raw Material in Petrochemical Process". p. 98, col. L; XP002123394.

*Primary Examiner*—Michael L. Shippen
*Attorney, Agent, or Firm*—Sughrue, Mion, Zinn, Macpeak & Seas, PLLC

[57] ABSTRACT

A process for producing dichloroacetoxypropane comprising reacting allyl acetate with chlorine in a gaseous phase in the presence of a catalyst. The dichloroacetoxypropane obtained may be converted to dichloropropanol and epichlorohydrin.

14 Claims, No Drawings

PROCESS FOR PRODUCING DICHLOROACETOXYPROPANE AND DERIVATIVES THEREOF

CROSS REFERENCE TO RELATED APPLICATIONS

This application is an application filed under 35 U.S.C. §111(a) claiming benefit pursuant to 35 U.S.C. §119(e)(1) of the filing date of the Provisional Application 60/082,625 filed Apr. 22, 1998, pursuant to 35 U.S.C. §111(b).

BACKGROUND OF THE INVENTION

1. Field of the Invention

The present invention relates to a process for the production of dichloroacetoxypropane and derivatives thereof which are raw materials for useful organic products.

2. Description of the Related Art

The term "dichloroacetoxypropane" as used herein refers to 2,3-dichloro-1-acetoxypropane, 1,3-dichloro-2-acetoxypropane or a mixture thereof. Further, the term "dichloropropanol" as used herein refers to 2,3-dichloro-1-propanol, 1,3-dichloro-2-propanol or a mixture thereof.

A process for producing dichloroacetoxypropane by reacting allyl acetate with chlorine in a liquid phase is described, for example, in Khim. Prom., No. 5, 277–280 (1981), Khim. Prom., No. 6, 328–335 (1982) and Japanese Examined Patent Publication (Kokoku) No. 52-16091. The reaction is represented by the following formula.

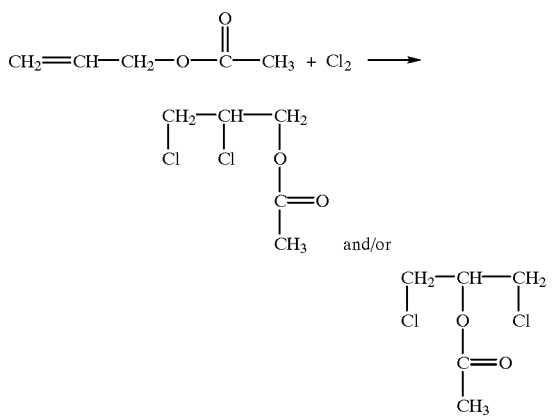

These conventional techniques all relate to the reaction in a liquid phase and use a metal salt such as a metal halide as a catalyst. However, when a metal salt is used as a catalyst, the catalyst must be separated and recovered after the reaction. Moreover, the metal salt dissolves into the reaction solution and the separation and recovery of the dissolved metal salt presents another problem. In order to prevent the metal salt dissolving, Japanese Examined Patent Publication No. 52-16091 proposes a supported catalyst in which a metal salt is supported on a support. However, it is still difficult to prevent the metal salt dissolving out of the support.

Furthermore, in all the above-described conventional techniques, the reaction of allyl acetate with chlorine is effected in the presence of an organic solvent. The use of an organic solvent has, however, a problem in that a recovery step therefor is necessary or loss of the organic solvent is caused at the time of recovery.

There is still another problem in that since the production of dichloroacetoxypropane by the reaction of allyl acetate with chlorine is an exothermic reaction, external cooling or the like is necessary in order to obtain dichloroacetoxypropane with high efficiency and this causes a loss of energy.

As a conventional technique for chlorination in a gaseous phase, a reaction of ethylene with chlorine is known (see, for example, U.S. Pat. No. 2,099,231). However, a method of producing dichloroacetoxypropane by reacting allyl acetate with chlorine in a gaseous phase has not hitherto been reported.

SUMMARY OF THE INVENTION

An object of the present invention is to overcome the defects of the liquid phase processes conventionally employed for the production of dichloroacetoxypropane, more specifically, problems such as the necessity of a step for separating and recovering a catalyst, the necessity of a step for recovering an organic solvent resulting from use of an organic solvent, the loss of the organic solvent during recovery or the loss of energy accompanying external cooling, and to provide an industrially more advantageous production process for dichloroacetoxypropane as well as an industrially more advantageous production process for a derivative of dichloroacetoxypropane, such as dichloropropanol or epichlorohydrin, using the above-described process.

As a result of extensive investigations to solve the above-described problems, the present inventors have found that the object of the present invention can be attained by a process for producing dichloroacetoxypropane, comprising reacting allyl acetate with chlorine in a gaseous phase in the presence of a catalyst. The present invention has been accomplished based on this finding. In other words, the present invention provides a process for producing dichloroacetoxypropane, comprising reacting allyl acetate with chlorine in a gaseous phase in the presence of a catalyst.

The present invention also provides a process for efficiently producing dichloroacetoxypropane by reacting allyl acetate with chlorine in a gaseous phase and then efficiently producing a derivative thereof, for example, a process for efficiently producing dichloropropanol from the resulting dichloroacetoxypropane and a process for further producing epichlorohydrin in good efficiency.

DESCRIPTION OF THE PREFERRED EMBODIMENTS

The present invention is described in detail below.

Allyl acetate for use in the present invention may be any commercially or industrially available allyl acetate and is not particularly limited.

Chlorine for use in the present invention may be any commercially or industrially available chlorine and is not particularly limited.

The catalyst for use in the production of dichloroacetoxypropane according to the present invention is preferably a catalyst containing at least one metal selected from the metals of Groups 1 to 15 of the long-form Periodic Table or at least one metal compound containing the at least one metal. Examples of the metal element of the metal or metal compound include Group 1 elements of the long-form Periodic Table, such as Na, K and Cs, Group 2 elements such as Mg and Ca, Group 3 elements such as Sc, lanthanoid elements and actinoid elements, Group 4 elements such as Ti and Zr, Group 5 elements such as V and Nb, Group 6 elements such as Cr and W, Group 7 elements such as Mn and Re, Group 8 elements such as Fe and Ru, Group 9 elements such as Co and Rh, Group 10 elements such as Ni and Pd, Group 11 elements such as Cu and Ag, Group 12 elements such as Zn and Cd, Group 13 elements such as Al and Ga, Group 14 elements such as Si and Sn, and Group 15 elements such as Sb and Bi, but the present invention is by no means limited thereto.

Specific examples of the metal compound include halides, oxides, carbonates, phosphates, nitrates, sulfates, oxyhalides, basic carbonates, hydroxides, carboxylates and organic metal complexes of the above-described metals, however, the present invention is by no means limited thereto. Of these, halides and oxides are preferred.

Examples of the halogen of the halides or oxyhalides include fluorine, chlorine, bromine and iodine. Of these, chlorine is preferred.

The catalyst can be used in any known form and is not particularly limited. The catalyst is preferably a support type, a coprecipitation type or an ion exchange type, more preferably a support type in which at least one metal selected from the metals of Groups 1 to 15 of the long-form Periodic Table or at least one metal compound containing the at least one metal is supported on a support. The metal or metal compound per se may of course be used as a catalyst as it is.

The metal or metal compound to be used for the catalyst in the present invention may suitably have a concentration of from 0.01 to 100 wt %, preferably from 0.1 to 50 wt %, based on the total weight of the catalyst.

In the case of a supported catalyst, specific examples of the support include single oxides such as alumina, zirconia, titania, niobia, silica and magnesia, complex oxides such as silica alumina, and zeolite, heteropolyacids, activated carbon and polymers, but the support is not particularly limited thereto. The support may contain the same element as the at least one metal or metal compound used for the catalyst.

The supported catalyst can be prepared by a known process, for example, a process for impregnating a metal compound into a support. More specifically, for supporting a metal compound on a support, the metal compound is dissolved in an appropriate solvent such as water, alcohol, hydrochloric acid or aqueous ammonia, in an amount such that the support can absorb the solution. To the resulting solution, a support having an appropriate particle size is added and, after being impregnated with the solution, the support is dried. The drying may be performed either under normal pressure or a reduced pressure. For example, in the case of drying the catalyst under a reduced pressure, the drying may be performed in a vacuum dryer at from 20 to 300° C. The drying is preferably continued until the catalyst reaches a constant weight.

The dried supported catalyst may be used as it is in the reaction or may be calcined before use. The calcination may be performed in an atmosphere of nitrogen, carbon dioxide, air, oxygen, hydrogen or the like, however, the atmosphere is not particularly limited as far as it matches the purpose. For example, in the case of a catalyst containing a compound of at least one metal selected from the metals of Groups 1 to 15 of the long-form Periodic Table, the calcination may be performed in an atmosphere inactive to the catalyst and is preferably performed in a nitrogen atmosphere.

The catalyst containing the metal compound may be prepared by any known process. For example, the catalyst may be prepared by calcining and reducing a catalyst containing a compound of at least one metal selected from the metals of Groups 1 to 15 of the long-form Periodic Table in an atmosphere containing a reducing agent such as hydrogen, paraffin or olefin, however, the present invention is by no means limited thereto.

The calcination temperature is not particularly limited, however, it is preferably a temperature higher than the reaction temperature. The calcination time is also not particularly limited, but the calcination is preferably continued until the catalyst reaches a constant weight.

The catalyst used in the present invention may have any shape such as a tablet, a ring, a sphere, a microsphere or an extrusion but is not particularly limited. The shaping may be performed by any known method such as compression molding, extrusion molding or spray drying granulation. Furthermore, the catalyst may be used after being blended with an inactive filler.

As the filler, there may be mentioned an inactive solid material such as glass beads, silicon carbide or silicon nitride, but is not limited thereto.

When the reaction is performed according to the invention, even if the external temperature is constant, the temperature of the reaction mixture may locally be raised by local heat generation due to, for example, the process of the reaction at a certain zone of the catalyst layer. As a result, there may be caused problems such as the increase of by-products and reduction of catalyst life. In such a case, the local heat generation may be inhibited by blending and diluting the catalyst with the above-mentioned filler.

The blending of the catalyst with the filler may be carried out by any known method, such as a method of uniformly blending or a method of varying the blending ratio of the catalyst and the filler with respect to the flowing direction of the reaction gas mixture, but is not limited thereto.

The filler may have any shape such as a tablet, a ring, a sphere, a microsphere or an extrusion, but is not limited thereto. The shape may be the same as or different from that of the catalyst.

In the present invention, a condition such that dichloroacetoxypropane (e.g., 2,3-dichloro-1-acetoxypropane (boiling point: 191 to 192° C./100.7 kPa) and/or, 1,3-dichloro-2-acetoxypropane (boiling point: 195° C./101.3 kPa)) is in the gaseous state is preferred for the gaseous phase reaction to proceed smoothly. From the point of view of the reaction result, lowering of the reaction heat, separation of the reaction product from raw materials after the reaction and execution form, a diluent is preferably added.

The diluent is not particularly limited as far as it does not inhibit the production of dichloroacetoxypropane, but an inert gas is suitably used. The inert gas is not particularly limited and examples of the inert gas which can be used include nitrogen, carbon dioxide, helium and argon, however, the present invention is not limited thereto by any means. Of those mentioned, nitrogen is preferred.

With respect to the raw material gas for use in the production of dichloroacetoxypropane, the composition may be selected from the range such that allyl acetate is from 0.01 to 99.99 mol %, chlorine is from 0.0001 to 60 mol % and the diluent is from 0 to 99.99 mol %.

For achieving smooth gaseous phase reaction, the above-described composition of the raw material gas is preferably selected so that dichloroacetoxypropane produced can be kept in a gaseous state. More specifically, the composition of the raw material gas is preferably selected such that the partial pressure of dichloroacetoxypropane produced becomes lower than the saturated vapor pressure of dichloroacetoxypropane at the reaction temperature.

The molar ratio of chlorine to allyl acetate (chlorine/allyl acetate) may suitably be from 0.001 to 1.5, preferably from 0.01 to 1.0. If the molar ratio of chlorine/allyl acetate exceeds 1.5, a side reaction such as substitution may occur with the excess chlorine or recovery of a large amount of unreacted chlorine may be disadvantageously needed, whereas if the molar ratio of chlorine/allyl acetate is less than 0.001, there may arise a problem in that a large amount of allyl acetate must be recovered.

In the present invention, the molar ratio of the diluent to the chlorine (diluent/chlorine) may suitably be from 0 to 2,000, preferably from 0 to 1,000, however, the present invention is by no means limited thereto.

The raw material gas may suitably have a space velocity of from 100 to 12,000 $hr^{-1}$, preferably from 300 to 8,000 $hr^{-1}$, however, the present invention is by no means limited thereto.

In the process of the present invention, the reaction temperature at the time of producing dichloroacetoxypropane may suitably be from 70 to 300° C., preferably from 80 to 250° C. If the reaction temperature exceeds 300° C., there may arise a problem such as increase of the reaction product by substitution with chlorine or reduction of the catalyst life due to by-production or accumulation of a high boiling point compound, whereas if the reaction temperature is lower than 70° C., there may arise a problem in that a large amount of diluent resulting from increase of the amount of the diluent used for maintaining the gaseous phase state must be recycled, the productivity decreases or reaction in a stable gaseous phase becomes difficult.

The heat generated as the reaction proceeds between allyl acetate and chlorine may be discharged from the system by warm water or heating medium, so that the reaction temperature can be maintained in a constant range. In this case, it is possible and useful to use the heat taken out by warm water or a heating medium as a heat source of other facilities.

The pressure at the time of producing dichloroacetoxypropane according to the process of the present invention may suitably be from 10 to 1,000 kPa, preferably from 50 to 500 kPa. If the reaction pressure is either lower than 10 kPa or higher than 1,000 kPa, the practice becomes industrially difficult and this is not preferred.

In practicing the present invention, the reaction system for the gaseous phase reaction of allyl acetate with chlorine may be any known system and is not particularly limited, however, a continuous flow system is preferred.

The form of the reaction vessel for use in the present invention is not particularly limited, however, a fixed bed reaction vessel or a fluidized bed reaction vessel is preferred.

In the present invention, the raw material gas may be introduced into a reaction vessel by any known method and the method is not particularly limited. For example, a method of introducing allyl acetate after previously vaporizing it may be used. Chlorine may be introduced by any method such as a method of introducing chlorine into a reaction vessel after previously combining it with allyl acetate or a method of separately introducing these members into a reaction vessel. A method of introducing allyl acetate and chlorine such that these can efficiently contact on a catalyst, for example, a method of previously mixing allyl acetate and chlorine in a static mixer (see, *Kagaku Sochi (Chemical Apparatus)*, May, 74–78 (1994)) and then introducing these into a catalyst, may be used, however, the present invention is by no means limited thereto.

The manner of adding the diluent for use in the present invention is not particularly limited and any known form may be used, for example, the diluent may be added to allyl acetate, may be added only to chlorine or may be added to both of allyl acetate and chlorine.

For collecting dichloroacetoxypropane from the gas containing dichloroacetoxypropane produced in the above-described reaction vessel, any known method may be used. For example, by cooling the outlet of the reaction vessel, the gas component and the liquid component containing dichloroacetoxypropane as a product can be separated from each other and by distilling and purifying this liquid component containing dichloroacetoxypropane, dichloroacetoxypropane can be obtained.

In the case of using an inert gas as the diluent, the inert gas after separating dichloroacetoxypropane therefrom may be re-used by circulating it as it is or after purification. When allyl acetate is used in excess to chlorine, unreacted allyl acetate may be contained in the liquid component depending on the cooling temperature, but this can be re-used after separating it from dichloroacetoxypropane by distillation. Also, after concentrating only the objective dichloroacetoxypropane by setting the cooling temperature at a higher temperature, the unreacted allyl acetate in the gaseous state can be re-used by circulating it as it is or after purification.

Dichloroacetoxypropane produced by the process of the present invention may be a mixture of 2,3-dichloro-1-acetoxypropane and 1,3-dichloro-2-acetoxypropane. The dichloroacetoxypropane produced may have a compositional ratio in mol % such that 2,3-dichloro-1-acetoxypropane is from 5 to 100 mol % and 1,3-dichloro-1-acetoxypropane is from 0 to 95 mol %. These two isomers can be separated by a known method or can be separated by distillation or the like, however, the separation method is not limited thereto.

Depending on the use of dichloroacetoxypropane, for example, when it is used for the production of a derivative thereof such as dichloropropanol or epichlorohydrin, the dichloroacetoxypropane obtained by the above-described reaction can be used as a starting material for the next step without separating these two isomers.

A production process of dichloropropanol or epichlorohydrin using the dichloroacetoxypropane produced by the present invention is described below. Dichloropropanol and epichlorohydrin are compounds useful as a raw material for producing various compounds, as a solvent, as a starting material of epoxy resin or synthetic rubber, or as a stabilizer of chlorinated rubber.

The production process of dichloropropanol comprises the following first and second steps and the production process of epichlorohydrin comprises the following first to third steps.

First step:

A step of reacting allyl acetate with chlorine in a gaseous phase in the presence of a catalyst to produce dichloroacetoxypropane.

Second step:

A step of subjecting the dichloroacetoxypropane obtained in the first step to hydrolysis or alcoholysis to produce dichloropropanol.

Third step:

A step of dehydrochlorinating the dichloropropanol obtained in the second step to produce epichlorohydrin.

The first step is described in detail above in connection with the production method of dichloroacetoxypropane. The second and third steps are described in detail below.

The second step is a step of subjecting the dichloroacetoxypropane obtained according to the present invention to hydrolysis or alcoholysis to produce dichloropropanol.

The hydrolysis or alcoholysis of dichloroacetoxypropane can be performed by a known method and the method is not particularly limited. For example, the method described in *Khim. Prom.*, No. 6, 328–335 (1982) may be preferably used, where dichloroacetoxypropane is hydrolyzed or alcoholyzed using an acid catalyst such as hydrochloric acid, sulfuric acid or a cation exchange resin, to produce dichloropropanol.

In the case of hydrolysis, the molar ratio of water to dichloroacetoxypropane (water/dichloroacetoxypropane) may suitably be from 0.5 to 20.0, preferably from 1.0 to 10.0.

In the case of alcoholysis, the molar ratio of alcohol to dichloroacetoxypropane (alcohol/dichloroacetoxypropane) may suitably be from 0.5 to 20, preferably from 1.0 to 10.

Examples of the alcohol used for alcoholysis include methanol, ethanol, n-propanol, isopropanol, n-butanol, isobutanol, t-butanol and allyl alcohol, however, the present invention is by no means limited thereto. More preferred is allyl alcohol.

When allyl alcohol is used for the alcoholysis, allyl acetate is produced along with dichloropropanol. This dichloropropanol can be converted to epichlorohydrin at the third step. On the other hand, allyl acetate can be recycled to the first step to be used as a raw material for dichloroacetoxypropane. When an alcohol other than allyl alcohol is used for the alcoholysis, there may arise a problem such as of the supply balance of dichloropropanol or epichlorohydrin with the concurrently produced acetate ester. For example, when butanol is used, there may arise a problem such as of the supply balance of dichloropropanol or epichlorohydrin with butyl acetate, but the problem may be prevented when using allyl alcohol.

Allyl alcohol used for the alcoholysis according to the present invention may be either anhydrous or hydrous allyl alcohol. In the case of the alcoholysis by hydrous allyl alcohol, the produced allyl acetate forms some azeotropic components with unreacted allyl alcohol and water. Furthermore, dichloroacetoxypropane is hydrolyzed with water contained in hydrous allyl alcohol to produce acetic acid. It is possible to separate allyl acetate, unreacted allyl alcohol, water and acetic acid, as a low boiling point component in the reaction system, from dichloropropanol and unreacted dichloroacetoxypropane. Then, allyl acetate, hydrous allyl alcohol and acetic acid can be separated from the low boiling point component and purified by any known method. For example, the separation and purification may be effected according to the distillation and two-phase separation described in Japanese Examined Patent Publication (Kokoku) No. 1-20137. The separated and purified allyl acetate may be recycled to the first step, and hydrous allyl alcohol and acetic acid may be recycled to the second step.

The reaction temperature in the second step is not particularly limited and it is preferably from 40 to 200° C., more preferably from 60 to 180° C.

The reaction in the second step may be performed in any known system, and specific examples of preferred reaction systems include a batch system, a semi-continuous system and a continuous system, however, the present invention is by no means limited thereto.

Dichloropropanol produced in the second step can be separated and purified by any known method. For example, the dichloropropanol is preferably separated and purified by distillation in the same manner as in the method described in Japanese Examined Patent Publication (Kokoku) No. 7-25711, however, the present invention is by no means limited thereto.

The third step is a step of dehydrochlorinating the dichloropropanol obtained in the second step to produce epichlorohydrin.

The third step can be performed by any known method. For example, epichlorohydrin is preferably produced by reacting dichloropropanol with an aqueous alkali solution or alkali suspension in the same manner as in the method described in Japanese Unexamined Patent Publication (Kokai) No. 60-258172, however, the present invention is by no means limited thereto.

The alkaline compound used in the third step is not particularly limited. Examples thereof include an aqueous solution and suspension of calcium hydroxide, sodium hydroxide, potassium hydroxide, sodium carbonate or potassium carbonate, however, the present invention is by no means limited thereto.

The amount of the alkaline compound used is not particularly limited, however, the alkaline compound is preferably used in an amount of from 1.0 to 1.5 equivalent, more preferably from 1.03 to 1.3 equivalent, per 1 mol of dichloropropanol.

The reaction of the third step may be performed by any known method. For example, the reaction is preferably performed by:

(1) a method of supplying an aqueous alkali solution or alkali suspension of the raw material of dichloropropanol from the top of a plate distillation column and blowing steam from the bottom to strip epichlorohydrin produced by the reaction while subjecting to azeotropic distillation (boiling point: 88° C.) with water; in this method, an inert gas such as nitrogen may be accompanied in addition to steam to increase the stripping effect;

(2) a method of mixing dichloropropanol or an aqueous solution thereof with an aqueous alkali solution or alkali suspension in a liquid phase and reacting the mixture while stirring; or (3) a method of allowing an inactive solvent substantially insoluble in water to be present together and performing reaction while extracting epichlorohydrin produced into the solvent.

The methods (2) and (3) may be performed either in a batch system or continuous system. In the case of a continuous system, a mixing tank-type reaction, a flow-type reaction in a tower reaction vessel or the like may be used. In the case of a flow-type reaction in a tower reaction vessel, dichloropropanol or a solution thereof and an aqueous alkali solution or alkali suspension may flow concurrently or countercurrently while coming into contact, to thereby effect reaction. The reaction methods (2) and (3) may be combined, for example, so that one method is used until the reaction proceeds to a certain level and then the other method is used to allow the reaction to proceed further.

The amount of steam used for stripping epichlorohydrin produced in the third step may suitably be such that the overhead product composition has a ratio by weight of water/epichlorohydrin of from 0.5 to 3.5, preferably from 1.0 to 2.5. As the amount of steam becomes larger, the selectivity of epichlorohydrin increases, however, if it is too large, high steam consumption may result. Accordingly, the amount used in practice is limited. On the other hand, if the amount of steam is too small, the stripping effect may decrease and the selectivity of epichlorohydrin may be reduced.

The reaction temperature in the third step is not particularly limited but it is preferably from 40 to 110° C., more preferably from 60 to 100° C. As the reaction temperature becomes lower, the selectivity of epichlorohydrin elevates, however, since the reaction rate may decrease, the reaction time may be prolonged. The reaction pressure in the third step is not particularly limited but it is preferably from 10 to 200 kPa.

The present invention is described in greater detail below by referring to the Examples and Comparative Examples, however, the present invention is by no means limited to these Examples.

Catalyst Preparation Process 1

5 g of a metal compound was dissolved in 25 g of methanol and 95 g of a support was added to be impregnated with the solution at room temperature for 30 minutes. Thereafter, the impregnated matter was vacuum dried at 150° C. for 3 hours. The dried matter was calcined at 500° C. for 3 hours in a nitrogen stream to obtain a catalyst as a metal compound (5 wt %)/support (95 wt %).

Catalyst Preparation Process 2

5 g of a metal compound was dissolved in 22 g of water and 95 g of a support was added to be impregnated with the solution at room temperature for 30 minutes. Thereafter, the impregnated matter was vacuum dried at 150° C. for 3 hours. The dried matter was calcined at 500° C. for 3 hours in a nitrogen stream to obtain a catalyst as a metal compound (5 wt %)/support (95 wt %).

Catalyst Preparation Process 3

5 g of a metal compound was dissolved in 25 g of methanol and 95 g of a support was added to be impregnated with the solution at room temperature for 30 minutes. Thereafter, the impregnated matter was vacuum dried at 150° C. for 3 hours. The dried matter was calcined at 200° C. for 3 hours in a nitrogen stream to obtain a catalyst as a metal compound (5 wt %)/support (95 wt %).

Catalyst Preparation Process 4

5 g of a metal compound was dissolved in 25 g of methanol and 95 g of a support was added to be impregnated with the solution at room temperature for 30 minutes. Thereafter, the impregnated matter was vacuum dried at 150° C. for 3 hours. The dried matter was calcined at 270° C. for 3 hours in a nitrogen stream to obtain a catalyst as a metal compound (5 wt %)/support (95 wt %).

Catalyst Preparation Process 5

5 g of a metal compound was dissolved in 38 g of a 28 wt % aqueous ammonia and 95 g of a support was added to be impregnated with the solution at room temperature for 30 minutes. Thereafter, the impregnated matter was vacuum dried at 150° C. for 3 hours. The dried matter was calcined at 400° C. for 3 hours in a nitrogen stream to obtain a catalyst as a metal compound (5 wt %)/support (95 wt %).

Catalyst Preparation Process 6

5 g of metal compound A and 5 g of metal compound B were dissolved in 24 g of methanol and 90 g of a support was added to be impregnated with the solution at room temperature for 30 minutes. Thereafter, the impregnated matter was vacuum dried at 150° C. for 3 hours. The dried matter was calcined at 200° C. for 3 hours in a nitrogen stream to obtain a catalyst as metal compound A (5 wt %)+metal compound B (5 wt %)/support (90 wt %).

Catalyst Preparation Process 7

5.2 g of metal compound A and 1 g of metal compound B were dissolved in 24 g of methanol and 93.8 g of a support was added to be impregnated with the solution at room temperature for 30 minutes. Thereafter, the impregnated matter was vacuum dried at 150° C. for 3 hours. The dried matter was calcined at 200° C. for 3 hours in a nitrogen stream to obtain a catalyst as metal compound A (5.2 wt %)+metal compound B (1.0 wt %)/support (93.8 wt %).

EXAMPLE 1

Using $MnCl_2$ as the metal compound and $ZrO_2$ (particle size: from 0.5 to 2.0 mm) as the support, a catalyst was prepared by the catalyst preparation process 1.

17 ml of the catalyst was filled in an upright glass-made reaction vessel having an inner diameter of 14 mm and a length of 15 cm and equipped with glass tubing for the measurement of temperature.

The reaction vessel was heated to 90° C. with a heating medium to adjust the pressure to 101.3 kPa. Then, a raw material gas comprising 0.8 mol % of chlorine, 3.2 mol % of allyl acetate and 96.0 mol % of nitrogen was introduced into the reaction vessel at a space velocity of 3,671 $h^{-1}$ and reacted. The allyl acetate was previously vaporized through a vaporizer set at 90° C.

Thereafter, the outlet of reaction vessel was cooled, the unreacted chlorine gas was quenched with an aqueous sodium thiosulfate solution, and the distillate condensed by the cooling was collected. The distillate obtained was analyzed by gas chromatography to determine the yield of dichloroacetoxypropane (based on the raw material chlorine) and the compositional ratio (mol %) thereof. The measurement was performed using the maximum temperature of the catalyst layer in the reaction vessel as the reaction temperature. The results obtained are shown in Table 1.

EXAMPLE 2

Reaction was performed in the same manner as in Example 1 except for using $CuCl_2$ as the metal compound. The results are shown in Table 1.

EXAMPLE 3

Reaction was performed in the same manner as in Example 1 except for using $FeCl_2$ as the metal compound. The results are shown in Table 1.

EXAMPLE 4

Reaction was performed in the same manner as in Example 1 except for using $CoCl_2$ as the metal compound. The results are shown in Table 1.

EXAMPLE 5

Reaction was performed in the same manner as in Example 1 except for using $CaCl_2$ as the metal compound. The results are shown in Table 1.

EXAMPLE 6

Reaction was performed in the same manner as in Example 1 except for using $CrCl_2$ as the metal compound. The results are shown in Table 1.

EXAMPLE 7

Reaction was performed in the same manner as in Example 1 except for using CsCl as the metal compound. The results are shown in Table 1.

EXAMPLE 8

Reaction was performed in the same manner as in Example 1 except for using a catalyst prepared according to catalyst preparation process 2 by using NiCl$_2$ as the metal compound, ZrO$_2$ (particle size: from 0.5 to 2.0 mm) as the support. The results are shown in Table 1.

EXAMPLE 9

Reaction was performed in the same manner as in Example 8 except for using LaCl$_3$ as the metal compound. The results are shown in Table 1.

EXAMPLE 10

Reaction was performed in the same manner as in Example 1 except for using a catalyst prepared according to catalyst preparation process 3 by using SnCl$_2$ as the metal compound, ZrO$_2$ (particle size: from 0.5 to 2.0 mm) as the support. The results are shown in Table 1.

EXAMPLE 11

Reaction was performed in the same manner as in Example 10 except for using ZnCl$_2$ as the metal compound. The results are shown in Table 1.

EXAMPLE 12

Reaction was performed in the same manner as in Example 10 except for using BiCl$_3$ as the metal compound. The results are shown in Table 1.

EXAMPLE 13

Reaction was performed in the same manner as in Example 1 except for using a catalyst prepared according to catalyst preparation process 4 by using FeCl$_3$ as the metal compound, ZrO$_2$ (particle size: from 0.5 to 2.0 mm) as the support. The results are shown in Table 1.

EXAMPLE 14

Reaction was performed in the same manner as in Example 1 except for using CuCl as the metal compound, ZrO$_2$ (particle size: from 0.5 to 2.0 mm) as the support and a catalyst prepared according to the catalyst preparation process 5. The results are shown in Table 1.

EXAMPLE 15

A catalyst was prepared in the same manner as in the catalyst preparation process 1 except for using 5 g of MnCl$_2$ dissolved in 90 g of methanol as the metal compound and 95 g of Al$_2$O$_3$ (particle size: 1.6 mm) as the support. Then, reaction was performed in the same manner as in Example 1 except for using this catalyst. The results are shown in Table 1.

EXAMPLE 16

Reaction was performed in the same manner as in Example 1 except for using ZrO$_2$ (particle size: from 0.5 to 2.0 mm) as the catalyst. The results are shown in Table 1.

EXAMPLE 17

Reaction was performed in the same manner as in Example 1 except for using Al$_2$O$_3$ (particle size: 1.6 mm) as the catalyst. The results are shown in Table 1.

EXAMPLE 18

Reaction was performed in the same manner as in Example 1 except for using Nb$_2$O$_5$ (particle size: from 0.5 to 2.0 mm) as the catalyst. The results are shown in Table 1.

EXAMPLE 19

Reaction was performed in the same manner as in Example 1 except for heating the reaction vessel to 110° C. with a heat medium and setting the vaporizer at 110° C. The results are shown in Table 1.

EXAMPLE 20

Reaction was performed in the same manner as in Example 1 except for heating the reaction vessel to 130° C. with a heat medium and setting the vaporizer at 130° C. The results are shown in Table 1.

EXAMPLE 21

Reaction was performed in the same manner as in Example 1 except for introducing a raw material gas comprising 5 mol % of chlorine, 5 mol % of allyl acetate and 90 mol % of nitrogen at a space velocity of 600 h$^{-1}$ into the reaction vessel. The results are shown in Table 1.

EXAMPLE 22

Reaction was performed in the same manner as in Example 1 except for introducing a raw material gas comprising 1 mol % of chlorine and 99 mol % of allyl acetate at a space velocity of 300 h$^{-1}$, heating the reaction vessel to 130° C. with a heat medium, and setting the vaporizer at 130° C. The results are shown in Table 1.

EXAMPLE 23

Reaction was performed in the same manner as in Example 1 except for using a catalyst prepared according to catalyst preparation process 6 by using ZnCl$_2$ as metal compound A, MnCl$_2$ as metal compound B and ZrO$_2$ (particle size: from 0.5 to 2.0 mm) as the support. The results are shown in Table 1.

EXAMPLE 24

Reaction was performed in the same manner as in Example 1 except for using a catalyst prepared according to catalyst preparation process 7 by using ZnCl$_2$ as metal compound A, MnCl$_2$ as metal compound B and ZrO$_2$ (particle size: from 0.5 to 2.0 mm) as the support. The results are shown in Table 1.

EXAMPLE 25

Reaction was performed in the same manner as in Example 1 except for filling a catalyst prepared according to catalyst preparation process 3 by using ZnCl$_2$ as the metal compound and ZrO$_2$ (particle size: from 0.5 to 2.0 mm) as the support in the reaction vessel and introducing a raw material gas comprising 1.2 mol % of chlorine, 3.1 mol % of allyl acetate and 95.7 mol % of nitrogen into the reaction vessel at a space velocity of 3,688 h$_{-1}$. The results are shown in Table 1.

EXAMPLE 26

Reaction was performed in the same manner as in Example 25 except for filling a catalyst prepared according to catalyst preparation process 6 by using ZnCl$_2$ as metal compound A, MnCl$_2$ as metal compound B and ZrO$_2$ (particle size: from 0.5 to 2.0 mm) as the support in the reaction vessel. The results are shown in Table 1.

EXAMPLE 27

Reaction was performed in the same manner as in Example 25 except for filling a catalyst prepared according to catalyst preparation process 6 by using $ZnCl_2$ as metal compound A, $MnCl_2$ as metal compound B and $Al_2O_3$ (particle size: 1.6 mm) as the support in the reaction vessel. The results are shown in Table 1.

EXAMPLE 28

Reaction was performed in the same manner as in Example 1 except for filling a catalyst prepared as described in Example 26 in the reaction vessel, heating the reaction vessel to 120° C. with a heating medium, setting the vaporizer at 120° C. and introducing a raw material gas comprising 2.3 mol % of chlorine, 5.9 mol % of allyl acetate and 91.8 mol % of nitrogen into the reaction vessel at a space velocity of 1,923 $h^{-1}$. The results are shown in Table 1.

EXAMPLE 29

Reaction was performed in the same manner as in Example 1 except for filling a catalyst prepared as described in Example 26 in the reaction vessel, heating the reaction vessel to 120° C. with a heating medium, setting the vaporizer at 120° C. and introducing a raw material gas comprising 4.3 mol % of chlorine, 10.9 mol % of allyl acetate and 84.8 mol % of nitrogen into the reaction vessel at a space velocity of 1,040 $h^{-1}$. The results are shown in Table 1.

EXAMPLE 30

Reaction was performed in the same manner as in Example 29 except for using a catalyst prepared as described in Example 27. The results are shown in Table 1.

EXAMPLE 31

Reaction was performed in the same manner as in Example 29 except for blending, as uniformly as possible, 5.7 ml of a catalyst prepared as described in Example 27 with 11.3 ml of glass beads (particle size: from 0.9 to 1.4 mm) as a filler, filling the blend in the reaction vessel and introducing a raw material gas comprising 4.3 mol % of chlorine, 10.9 mol % of allyl acetate and 84.8 mol % of nitrogen into the reaction vessel at a space velocity of 1,040 $h^{-1}$. The results are shown in Table 1.

EXAMPLE 32

Reaction was performed in the same manner as in Example 31 except for using 11.3 ml of silicon carbide (particle size: 2.0 mm) as the filler. The results are shown in Table 1.

Comparative Example 1

Reaction was performed in the same manner as in Example 1 except for filling 17 ml of glass beads (particle size: from 0.99 to 1.4 mm) into the reaction vessel in place of the catalyst. The results are shown in Table 1.

TABLE 1

| | Catalyst | Reaction Temperature (° C.) | Yield of Dichloroace-toxypropane (%) | Compositional Ratio (mol %) of Dichloroacetoxypropane | |
|---|---|---|---|---|---|
| | | | | 2,3-Dichloro-1-acetoxypropane | 1,3-Dichloro-2-acetoxypropane |
| Example 1 | $MnCl_2$ (5 wt %)/$ZrO_2$ (95 wt %) | 101 | 91.94 | 78.06 | 21.94 |
| Example 2 | $CuCl_2$ (5 wt %)/$ZrO_2$ (95 wt %) | 104 | 90.49 | 67.89 | 32.11 |
| Example 3 | $FeCl_2$ (5 wt %)/$ZrO_2$ (95 wt %) | 103 | 81.39 | 74.69 | 25.31 |
| Example 4 | $CoCl_2$ (5 wt %)/$ZrO_2$ (95 wt %) | 102 | 88.44 | 72.09 | 27.81 |
| Example 5 | $CaCl_2$ (5 wt %)/$ZrO_2$ (95 wt %) | 102 | 84.12 | 86.25 | 13.75 |
| Example 6 | $CrCl_2$ (5 wt %)/$ZrO_2$ (95 wt %) | 99 | 70.51 | 73.18 | 26.82 |
| Example 7 | $CsCl$ (5 wt %)/$ZrO_2$ (95 wt %) | 105 | 86.51 | 90.30 | 9.70 |
| Example 8 | $NiCl_2$ (5 wt %)/$ZrO_2$ (95 wt %) | 105 | 90.50 | 65.12 | 34.88 |
| Example 9 | $LaCl_3$ (5 wt %)/$ZrO_2$ (95 wt %) | 103 | 87.68 | 86.48 | 13.52 |
| Example 10 | $SnCl_2$ (5 wt %)/$ZrO_2$ (95 wt %) | 100 | 62.07 | 69.49 | 31.51 |
| Example 11 | $ZnCl_2$ (5 wt %)/$ZrO_2$ (95 wt %) | 105 | 98.76 | 79.93 | 20.07 |
| Example 12 | $BiCl_3$ (5 wt %)/$ZrO_2$ (95 wt %) | 108 | 95.68 | 84.21 | 15.79 |
| Example 13 | $FeCl_3$ (5 wt %)/$ZrO_2$ (95 wt %) | 106 | 80.74 | 81.41 | 18.59 |
| Example 14 | $CuCl$ (5 wt %)/$ZrO_2$ (95 wt %) | 103 | 81.21 | 68.44 | 31.56 |
| Example 15 | $MnCl_2$ (5 wt %)/$Al_2O_3$(95 wt %) | 105 | 87.29 | 76.47 | 23.53 |
| Example 16 | $ZrO_2$ | 99 | 67.86 | 75.16 | 24.84 |
| Example 17 | $Al_2O_3$ | 102 | 60.12 | 73.12 | 26.88 |
| Example 18 | $Nb_2O_5$ | 102 | 66.18 | 75.01 | 24.99 |
| Example 19 | $MnCl_2$ (5 wt %)/$ZrO_2$ (95 wt %) | 124 | 91.63 | 79.74 | 20.26 |
| Example 20 | $MnCl_2$ (5 wt %)/$ZrO_2$ (95 wt %) | 144 | 91.26 | 79.89 | 20.11 |
| Example 21 | $MnCl_2$ (5 wt %)/$ZrO_2$ (95 wt %) | 108 | 90.23 | 78.21 | 21.79 |
| Example 22 | $MnCl_2$ (5 wt %)/$ZrO_2$ (95 wt %) | 145 | 90.02 | 79.03 | 20.97 |
| Example 23 | $ZnCl_2$ (5 wt %) + $MnCl_2$ (5 wt %)/$ZrO_2$ (90 wt %) | 113 | 99.21 | 83.11 | 16.89 |
| Example 24 | $ZnCl_2$ (5.2 wt %) + $MnCl_2$ (1.0 wt %)/$ZrO_2$ (93.8 wt %) | 115 | 98.92 | 83.74 | 16.26 |
| Example 25 | $ZnCl_2$ (5 wt %) + $ZrO_2$ (95 wt %) | 117 | 96.81 | 79.50 | 20.50 |
| Example 26 | $ZnCl_2$ (5 wt %) + $MnCl_2$ (5 wt %)/$ZrO_2$ (90 wt %) | 127 | 98.54 | 83.77 | 16.23 |
| Example 27 | $ZnCl_2$ (5 wt %) + $MnCl_2$ (5 wt %)/$Al_2O_3$ (90 wt %) | 114 | 99.12 | 83.37 | 16.63 |
| Example 28 | $ZnCl_2$ (5 wt %) + $MnCl_2$ (5 wt %)/$ZrO_2$ (90 wt %) | 161 | 95.30 | 73.19 | 26.82 |

TABLE 1-continued

|  | Catalyst | Reaction Temperature (° C.) | Yield of Dichloroacetoxypropane (%) | Compositional Ratio (mol %) of Dichloroacetoxypropane | |
|---|---|---|---|---|---|
|  |  |  |  | 2,3-Dichloro-1-acetoxypropane | 1,3-Dichloro-2-acetoxypropane |
| Example 29 | $ZnCl_2$ (5 wt %) + $MnCl_2$ (5 wt %)/$ZrO_2$ (90 wt %) | 160 | 93.00 | 71.63 | 28.37 |
| Example 30 | $ZnCl_2$ (5 wt %) + $MnCl_2$ (5 wt %)/$Al_2O_3$ (90 wt %) | 157 | 95.96 | 75.86 | 24.14 |
| Example 31 | $ZnCl_2$ (5 wt %) + $MnCl_2$ (5 wt %)/$Al_2O_3$ (90 wt %) | 148 | 97.51 | 80.02 | 19.98 |
| Example 32 | $ZnCl_2$ (5 wt %) + $MnCl_2$ (5 wt %)/$Al_2O_3$ (90 wt %) | 148 | 98.40 | 79.49 | 20.51 |
| Comparative Example 1 | glass beads | 90 | 20.35 | 95.74 | 4.26 |

EXAMPLE 33
Production of dichloropropanol: Production of dichloropropanol by hydrolysis of dichloroacetoxypropane 400 g (2.34 mol) of dichloroacetoxypropane produced in Example 1, 126 g (7.02 mol) of water and 7.4 g of a 35 wt % hydrochloric acid were charged into a glass reaction vessel and heated at 90° C. for 5 hours under normal pressure. The reaction liquid obtained was distilled in a distillation column to distill the azeotropic component of water and dichloropropanol, water and acetic acid from the top and recover the bottom liquid containing dichloropropanol from the bottom. The bottom liquid obtained was further distilled to obtain 212 g (1.64 mol) of dichloropropanol. The yield of dichloropropanol was 70.3%. The compositional ratio thereof was such that 2,3-dichloro-1-propanol was 73.42 mol % and 1,3-dichloro-2-propanol was 26.58 mol %.

EXAMPLE 34
Production of dichloropropanol: Production of dichloropropanol by alcoholysis of dlchloroacetoxypropane with n-butanol 400 g (2.34 mol) of dichloroacetoxypropane produced in Example 1, 520 g (7.02 mol) of n-butanol and 7.4 g of a 35 wt % hydrochloric acid were charged into a glass-made reaction vessel and heated at 90° C. for 5 hours under normal pressure. The reaction liquid obtained was distilled in a distillation column to obtain 272 g (2.11 mol) of dichloropropanol. The yield of dichloropropanol was 90.2%. The compositional ratio thereof was such that 2,3-dichloro-1-propanol was 74.36 mol % and 1,3-dichloro-2-propanol was 25.64 mol %.

EXAMPLE 35
Production of dichloropropanol: Production of dichloropropanol by alcoholysis of dichloroacetoxypropane with 70 wt % aqueous allyl alcohol solution 75.0 g of dichloroacetoxypropane produced in Example 1, 50.9 g of allyl alcohol (commercial product) and 21.8 g of water (representing a 70 wt % aqueous allyl alcohol solution and an allyl alcohol/dichloroacetoxypropane mole ratio of 2.0), and 1.39 g of a 35 wt % hydrochloric acid as a catalyst were charged into a glass flask equipped with a Dimroth condenser, heated to 105° C. while stirring, and reacted under reflux for 3 hours. The reaction liquid was analyzed by gas chromatography. The product had a composition of 5.35 g of unreacted dichloroacetoxypropane, 52.12 g of produced dichloropropanol, 24.41 g of produced allyl acetate, 35.31 g of unreacted allyl alcohol and 22.80 g of water. Furthermore, it was found that 8.80 g of acetic acid was produced by the hydrolysis of allyl acetate. From the results, it was found that the conversion of dichloroacetoxypropane was 92.9%, the yield of dichloropropanol was 92.2% and the selectivity of thereof was 99.4% (on the basis of the raw material of dichloroacetoxypropane), and the yield of allyl acetate was 55.6% and the selectivity of thereof was 59.9% (on the basis of the raw material of dichloroacetoxypropane).

EXAMPLE 36

Reaction was performed in the same manner as in Example 35 except that the allyl alcohol/dichloroacetoxypropane mole ratio was 1.0. From the results of the gas chromatographic analysis of the reaction liquid after the reaction for 3 hours, it was found that the conversion of dichloroacetoxypropane was 83.9%, the yield of dichloropropanol was 82.2% and the selectivity of thereof was 98.0% (on the basis of the raw material of dichloroacetoxypropane).

EXAMPLE 37

Reaction was performed in the same manner as in Example 36 except that concentrated sulfuric acid was used as the catalyst.

From the results of the gas chromatographic analysis of the reaction liquid after the reaction for 3 hours, it was found that the conversion of dichloroacetoxypropane was 83.4%, the yield of dichloropropanol was 82.9% and the selectivity of thereof was 99.4% (on the basis of the raw material of dichloroacetoxypropane).

EXAMPLE 38
Production of dichloropropanol: Production of dichloropropanol by alcoholysis of dichloroacetoxypropane with anhydrous allyl alcohol Alcoholysis was effected as follows at an anhydrous allyl alcohol/dichloroacetoxypropane mole ratio of 1.0.

40.0 g of dichloroacetoxypropane produced in Example 1, 13.6 g of anhydrous allyl alcohol and 15 ml of a particulate cation exchange resin of particle sizes of 0.42 to 0.57 mm (Amberlite (trademark) IR-118 (H) type) were charged into a glass flask equipped with a Dimroth condenser, heated to 80° C. while stirring, and reacted for 3 hours. From the results of the gas chromatographic analysis of the reaction liquid, it was found that the reaction liquid contained 12.38 g of unreacted dichloroacetoxypropane, 20.56 g of produced dichloropropanol, 15.96 g of produced allyl acetate and 3.92 g of unreacted allyl alcohol. Since the reaction system contained no water, no production of acetic acid was found.

From the results, it was found that the conversion of dichloroacetoxypropane was 69.0%, the yield of dichloropropanol was 68.1% and the selectivity of thereof was 98.7% (on the basis of the raw material of dichloroacetoxypropane), and the yield of allyl acetate was 68.1% and the selectivity of thereof was 98.7% (on the basis of the raw material of dichloroacetoxypropane).

EXAMPLE 39

Production of dichloropropanol: Production of dichloropropanol by continuous alcoholysis of dichloroacetoxypropane with 70 wt % aqueous allyl alcohol solution Continuous alcoholysis with a fixed bed reaction vessel was effected as follows at an allyl alcohol/dichloroacetoxypropane mole ratio of 1.0.

10 ml of a particulate cation exchange resin (Amberlite (trademark) IR-118 (H) type) was filled in an upright glass tubing reaction vessel having an inner diameter of 14 mm, a length of 15 cm and a volume of about 18 ml and equipped with a side tubing at the upper portion, and the reaction vessel was heated to 85° C. with an oil bath, while setting the reaction vessel so that the outlet of the reaction vessel was outside of the oil bath.

3.27 g of 70 wt % aqueous allyl alcohol solution and 6.73 g of dichloroacetoxypropane, per hour, were introduced into the reaction vessel from the upper side tubing by metering pumps. A polytetrafluoroethylene tube was connected with the outlet of the reaction vessel and the reaction liquid flowing out was introduced into a flask of a recepter. The end portion of the polytetrafluoroethylene tube was set at the same level as the liquid level in the reaction vessel to keep the liquid level in the reaction vessel constant.

The reaction liquid in the receptor was analyzed, by gas chromatography, every hour. The weight of the liquid flowing out was 9.95 g per hour at the stationary state, and the flowing out liquid had a composition of 1.37 g of unreacted dichloroacetoxypropane and 3.75 g of produced dichloropropanol. From the results, it was found that the conversion of dichloroacetoxypropane was 79.6%, the yield of dichloropropanol was 73.9% and the selectivity of thereof was 92.8% (on the basis of the raw material of dichloroacetoxypropane).

EXAMPLE 40

Production of dichloropropanol: Distillation of reaction liquid obtained by alcoholysis with 70 wt % aqueous allyl alcohol solution A reaction liquid obtained by scaling up the procedure of Example 35 was distilled as follows.

297 g of a reaction liquid obtained by scaling up the procedure of Example 35 was charged in a 500 ml three-necked flask equipped with a dropping amount-controlling cock and a fractionating column having a reflux condenser and subjected to vacuum distillation under full reflux conditions. The distillation was continued while taking out a low boiling point component from the top of the fractionating column under a reduced pressure of 2.4 to 22 kPa until the low boiling point component ceased to distill.

The low boiling point component and a high boiling point component (the liquid retained in the flask) were analyzed by gas chromatography and using a Karl Fischer moisture meter. It was found that the low boiling point component mainly contained allyl acetate, allyl alcohol, water and acetic acid and contained a slight amount of dichloropropanol and dichloroacetoxypropane.

The liquid retained in the flask mainly contained dichloropropanol and unreacted dichloroacetoxypropane, the total amount of which comprised 99.6 wt % of the liquid retained in the flask.

EXAMPLE 41

Production of dichloropropanol: Production of dichloropropanol by alcoholysis with unhydrous allyl alcohol and separation of dichloropropanol.

A reaction liquid was obtained by scaling up the procedure of Example 38, the cation exchange resin of the catalyst was filtered off, and dichloropropanol was separated from the reaction liquid as follows.

2,000 g of a reaction liquid obtained by scaling up the procedure of Example 38 was treated in the same manner as in Example 40 using an apparatus similar to that used in Example 40, and a low boiling point component was taken out from the top of the fractionating column. The low boiling point component was a homogeneous solution in an amount of 725.7 g, and the retained liquid (high boiling point component) amounted to 1,232.4 g. The recovery was 97.9%.

When both components were analyzed by gas chromatography, it was found that the low boiling point component contained allyl acetate and unreacted allyl alcohol with a trace of dichloropropanol, while the retained liquid (high boiling point component) contained dichloropropanol and unreacted dichloroacetoxypropane with a trace of allyl acetate.

683.6 g of the low boiling point component obtained was subjected to distillation under normal pressure using an Oldershow distillation column. The low boiling point component from the top of the column was 239.5 g of an azeotropic component of allyl acetate and allyl alcohol, which was then recycled to the second step. The retained liquid of the low boiling point component was 436.4 g of allyl acetate, which was then recycled to the first step. The recovery was 98.9%.

Further, 1,109.2 g of the retained liquid of the high boiling point component was subjected to distillation using an Oldershow distillation column under a reduced pressure of 13.3 kPa. The liquid taken out was 687.2 g of dichloropropanol containing a trace of allyl acetate, which was then recycled to the third step. The liquid retained was 410.9 g of unreacted dichloroacetoxypropane, which was then recycled to the first step. The recovery was 99.0%.

EXAMPLE 42

Production of epichlorohydrin

The following dehydrochlorination column was used for performing dehydrochlorination reaction of dichloropropanol and for stripping to immediately separate epichlorohydrin produced from the reaction liquid.

The dehydrochlorination column body was made of glass and had an inner diameter of 55 mmΦ and a height of 1,500 mm. 10 porous plates each having 280 holes of 1 mm diameter were disposed at an interval of 100 mm and each porous plate had a 5 mm-depth downcomer. Under the lowest plate, a nozzle for blowing steam was provided and a constant amount of steam could be fed through a flowmeter. Above the uppermost plate, liquid feed nozzles were provided for feeding dichloropropanol and an aqueous alkali solution. A dichloropropanol solution and an aqueous alkali solution were supplied by metering pumps and mixed immediately before the liquid feed nozzle. From the top, a distillate was collected through a condenser. At the bottom, a 500 ml round bottom flask was fixed and a constant amount of solution was extracted by a metering pump to give a bottom solution in an amount of 40 ml.

Using the above-described apparatus, dichloropropanol obtained by the alcoholysis described in Example 34 and a 9.5 wt % aqueous $Ca(OH)_2$ slurry were supplied through the liquid feed nozzles at a rate of 83 g/h and 323 g/h, respectively, and at the same time, steam was blown through the steam blowing nozzle. The dichloropropanol concentration during feeding was 20 wt %. While extracting the waste from the bottom, the operation was continued for about 2 hours to stabilize the reaction system. One hour later, the top distillate and the bottom liquid were sampled and the compositions thereof were analyzed. The dichloropropanol conversion was 89.1% and epichlorohydrin selectivity was 97.0%. The temperature at the middle of the column was 100° C.

EXAMPLE 43

Production of epichlorohydrin

Reaction was performed in the same manner as in Example 42 except for using dichloropropanol obtained as described in Example 41. Thus, it was found that the conversion of dichloropropanol was 88.8% and the selectivity of epichlorohydrin was 97.3%.

According to the present invention, dichloroacetoxypropane can be obtained in a high yield and high selectivity without suffering from the defects conventionally encountered in the liquid phase method, namely, problems such as necessity of a step for separating and recovering a catalyst, loss of the energy accompanying the cooling, necessity of a step for recovering an organic solvent, or loss of the organic solvent by the recovery.

Furthermore, according to the present invention, a derivative of dichloroacetoxypropane can be effectively produced from allyl acetate by producing dichloroacetoxypropane in a high yield and high selectivity through reaction of allyl acetate with chlorine in a gaseous phase and then from the dichloroacetoxypropane obtained, producing a derivative thereof. More specifically, from dichloroacetoxypropane obtained, dichloropropanol and further epichlorohydrin can be produced with good efficiency.

What is claimed is:

1. A process for producing dichloroacetoxypropane comprising reacting allyl acetate with chlorine in a gaseous phase in the presence of a catalyst.

2. A process according to claim 1, wherein a diluent is added during the reaction of allyl acetate with chlorine.

3. A process according to claim 1, wherein the reaction of allyl acetate with chlorine is carried out at a temperature of 70 to 300° C.

4. A process according to claim 1, wherein the reaction of allyl acetate with chlorine is carried out under a pressure of 10 to 1,000 kPa.

5. A process according to claim 1, wherein the reaction of allyl acetate with chlorine is carried out at a temperature of 70 to 300° C. and under a pressure of 10 to 1,000 kPa.

6. A process according to claim 1, wherein the reaction of allyl acetate with chlorine is carried out at a molar ratio of chlorine to allyl acetate ranging from 0.001 to 1.5.

7. A process according to claim 1, wherein the catalyst comprises at least one metal selected from the metals of Groups 1 to 15 of the long-form Periodic Table or at least one metal compound containing said at least one metal.

8. A process according to claim 7, wherein said at least one metal compound is selected from metal halides and oxides.

9. A process according to claim 1, wherein the catalyst is a supported catalyst.

10. A process according to claim 1, wherein the catalyst is used blended with a filler.

11. A process for producing dichloropropanol comprising:

a first step of reacting allyl acetate with chlorine in a gaseous phase in the presence of a catalyst to produce dichloroacetoxypropane; and a second step of subjecting dichloroacetoxypropane obtained at the first step to hydrolysis or alcoholysis to produce dichloropropanol.

12. A process according to claim 11, wherein allyl alcohol is used for the alcoholysis.

13. A process for producing dichloropropanol comprising:

a first step of reacting allyl acetate with chlorine in a gaseous phase in the presence of a catalyst to produce dichloroacetoxypropane;

a second step of subjecting dichloroacetoxypropane obtained at the first step to hydrolysis or alcoholysis to produce dichloropropanol; and a third step of dehydrochlorinating dichloropropanol obtained at the second step to produce epishlorohydrin.

14. A process according to claim 13, wherein allyl alcohol is used for the alcoholysis.

* * * * *